United States Patent [19]

Falk

[11] Patent Number: 5,720,553
[45] Date of Patent: Feb. 24, 1998

[54] APPARATUS AND PROCESS FOR RAPID DIRECT DIP ANALYSIS OF MOLTEN IRON

[75] Inventor: Richard A. Falk, Hillsboro Beach, Fla.

[73] Assignee: Midwest Instrument Co., Inc., Hartland, Wis.

[21] Appl. No.: 556,762

[22] Filed: Nov. 2, 1995

[51] Int. Cl.$^6$ .................................................. G01N 25/02
[52] U.S. Cl. ................................................................ 374/26
[58] Field of Search ............................ 374/26, 139, 140; 73/864.53, 864.55, 864.58, 61.76

[56] References Cited

U.S. PATENT DOCUMENTS

| | | | |
|---|---|---|---|
| 3,693,449 | 9/1972 | Collins | 374/140 |
| 3,753,372 | 8/1973 | Collins | 73/864.56 |
| 3,813,944 | 6/1974 | Ryntz, Jr. et al. | |
| 4,261,202 | 4/1981 | Kawamoto et al. | |
| 4,699,014 | 10/1987 | Boron | 73/864.55 |

Primary Examiner—George M. Dombroske
Assistant Examiner—William L. Oen
Attorney, Agent, or Firm—Ryan, Maki, Mann & Hohenfeldt

[57] ABSTRACT

A process of determining carbon content silicon content and carbon equivalent of molten iron includes immersion into the molten iron of an analysis device having a mold chamber with a temperature measuring device extending into the chamber. The temperature measuring device is operatively connected to a device for continuously monitoring and recording the temperature. The mold chamber is provided with at least one inner wall of a metal which serves as a heat sink for molten metal introduced into the mold chamber. A layer of thermally insulating material surrounds the mold whereby heat transfer from molten metal into the chamber is minimized. The mold, after dipping is removed into the ambient environment. The temperature of the sample is continuously measured as it cools. The rate of cooling is continually computed and the derived rate of cooling curve is used to identify parameters of the sample from analysis of the rate of cooling over a period of time. Thus, values are determined for the carbon content, silicon content, and carbon equivalent and estimated nodularity count of the molten metal.

14 Claims, 6 Drawing Sheets

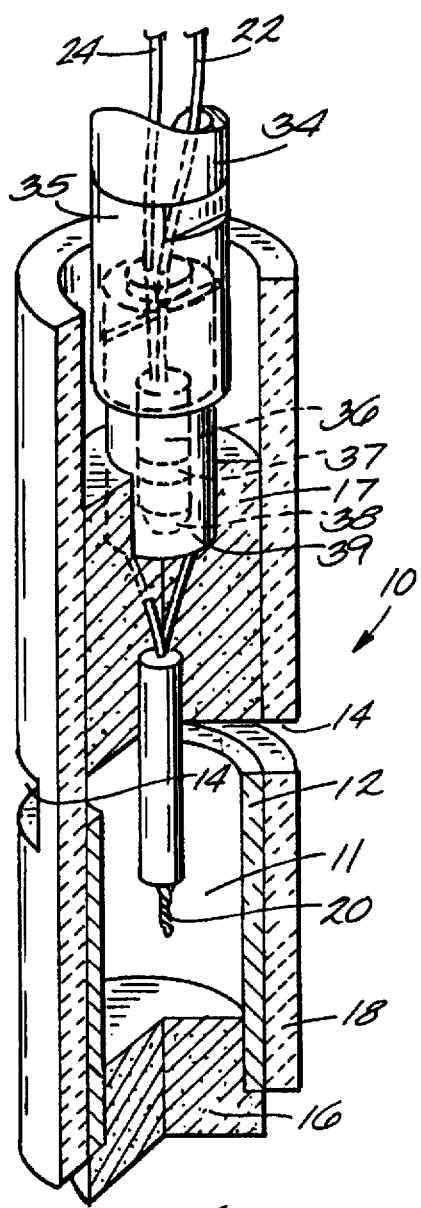
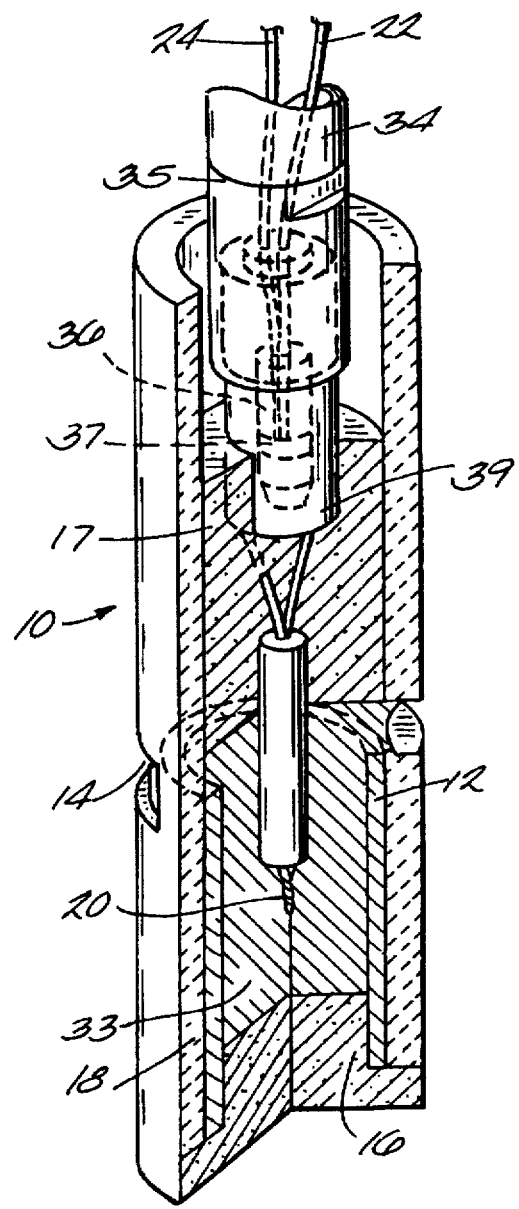

APPARATUS AND PROCESS FOR RAPID DIRECT DIP ANALYSIS OF MOLTEN IRON

FIELD OF THE INVENTION

The present invention relates to molten metal sampling. More particularly, the invention relates to analysis of molten metals such as iron for carbon content, silicon content, carbon equivalent and the accurate, reliable prediction of the nodularity count of treated ductile iron through thermal analysis data.

BACKGROUND OF THE INVENTION

Molten irons such as ductile iron are commonly analyzed for carbon, silicon or carbon equivalent by obtaining and thermally analyzing a small sample. It has been desirable to make an accurate analysis, and thus, in order to obtain samples wherein the carbon contained in the metal remains dissolved or interspersed in the metal in the form of a carbide rather than precipitating out in the form of graphite during a traditional analysis process which requires slow cooling for 1.5 to 3 minutes or more to reach the end of freezing point. It has been necessary to introduce additives such as tellurium, bismuth or antimony in order to deter graphite formation during this slow cooling. An example of this technique is set forth in Falk U.S. Pat. No. 4, 570,496 issued Feb. 18, 1986.

While the foregoing molds and procedures have enabled useful measurement of carbon contents or carbon equivalent (as defined in U.S. Pat. No. 3,546,921 issued Dec. 15, 1970), the existing procedures have suffered from the fact that the test procedures are time consuming and require spooning or ladling of a sample from an available source. A high superheat (ie., initial metal temperature above liquid eutectic or liquidus temperature) is needed in the thermal analysis sampler order to perform thermal analysis. Samples with adequate superheat are often not obtainable in modern automated foundries, thus making accurate analysis with traditional techniques difficult or impossible. Thus, a need has existed for devices and procedures for improving quality and expediting higher rates of production in the metal processing and refining industries.

In connection with the traditional carbon determination procedures, tellurium gives nuclei which traditional procedures require in order to avoid cooling patterns wherein supercooling occurs before the eutectic point and subsequently the sample requelesces at the eutectic point. The requelescence prevents accurate thermal analysis of the iron sample. Due to the time involved in these conventional procedures, an improved and more rapid procedure for accurately determining carbon content of ductile iron, in particular, has been needed. Also, because of the addition of Te or other additives, which remain in the samples as "impurities", the samples are not desirable for combustion or spectrographic analysis. Due to contamination by these toxic additives, the samples cannot be mixed back into the molten iron, but instead must be disposed of, for example, in a landfill.

SUMMARY OF THE INVENTION

It is a principal object of the present invention to provide a thermal analysis system which enables the rapid analysis of carbon, silicon, and carbon equivalent in molten iron. In accordance with an important aspect of the invention, a direct dip thermal analysis cup is provided which enables continuous monitoring of temperature and consequently analysis of the sampled iron. In accordance with a related aspect of the invention the direct dip thermal analysis cup includes a temperature monitoring device for continuous thermal analysis of the contents of the cup when removed from the molten metal with a sample thereof.

In accordance with a further aspect of the invention, the measurements of the thermal analysis device are continuously monitored by a data processor. In accordance with this aspect of the invention, continuous temperature measurements are utilized to compute the temperature and the rate of change of temperature in the cup over a period of time. The resultant curves can be plotted graphically.

In accordance with a further related aspect of the invention the temperature may be monitors for a brief period of time, such as approximately 30 seconds to arrive at an accurate analysis of the carbon, silicon or carbon equivalent in the metal. An accurate, reliable estimate of the nodularity count of the metal can also be generated. In accordance with a still further related aspect of invention the temperature/time data is continuously analyzed and monitored to compute or identify the liquidus and solidus temperatures of the sample and from this information to rapidly compute the carbon content, silicon content and the carbon equivalent as well as the approximate nodularity count. In accordance with a further related aspect of the invention accurate values for the carbon or carbon equivalent of the batch being tested are determined within a very brief period of time, for example 20 to 30 seconds after withdrawal of the sample. In accordance with still further related aspects of the invention other characteristics of the molten metal are identified from the derived temperature change rate curve. In accordance with further related aspects of the invention, changes in the rate of cooling over a brief period of time are measured and computed to determine the significant characteristics of the molten iron being analyzed. A further important characteristic thus obtained in accordance with the invention is a closely approximated nodularity count.

A highly important aspect of the invention involves providing of a sample mold in which a temperature measuring device is positioned and which encases the molten sample in a mass of metal which serves to cool the sample at a cooling rate which prevents graphite formation and requelescence in the sample, but which is, nonetheless cooled at a slow enough rate to provides meaningful data from which the carbon, silicon and carbon equivalent of the sample is determined. Another advantage of the invention relates to the fact that the solidified samples can be used for spectrographic analysis because, being free of additives, they are representative of the batch of iron being tested In accordance with further important aspects of the invention, the molten sample withdrawn is subjected to cooling at a rate faster that any requelescence of the sample could cause a temperature rise in the sample. In accord with a related aspect, a cooling rate of the sample between 0° and approximately 20° F. per second is maintained during the analytic procedures of this invention which determine carbon, silicon and carbon equivalents (in contrast with traditional procedures which require 0°/cooling rate for a short period in order to identify the eutectic point). The present invention requires only an identifiable fluctuation in the rate of cooling to identify the eutectic point. Cooling rates between −5° F. and 20° F. are maintained for nodularity count predictions.

An important advantage of the invention relates to the ability to obtain samples with necessary superheat from remote metal sources and small access openings. Thus accurate analysis can be performed in situations where prior art techniques cannot be used.

Briefly, the invention provides a process for analysis of molten iron which includes immersion into the molten iron of an analysis device having a mold chamber with a temperature measuring device or sensor, such as a thermocouple, extending into the chamber. The temperature sensor is operatively connected to a device, such as a data processor, for continuously monitoring and recording the temperature. The mold chamber is preferably provided with at least one inner wall of a metal which serves as a heat sink for molten metal introduced into the mold cavity. A layer of refractory thermally insulating material surrounds the mold whereby heat transfer from molten metal into the chamber is minimized, as is unwanted cooling when the mold, after dipping, is removed into the ambient environment.

The temperature of the sample is continuously measured as it cools. Analysis of the rate of cooling curve is used to identify parameters of the sample. Thus values for the carbon content, silicon content carbon equivalent and nodularity content of the molten metal are determined from the observations.

Further aspects and advantageous of the invention will be set forth in the following detailed description and claims and with reference to the accompanying drawings.

BRIEF DESCRIPTION OF THE DRAWINGS

FIG. 1 is a perspective view of a sampling device used in the practice of the invention with parts in section;

FIG. 2 is a perspective view of the device of FIG. 1 with parts in section showing a metal sample contained within said device;

DETAILED DESCRIPTION OF PREFERRED EMBODIMENTS

Figure 3:
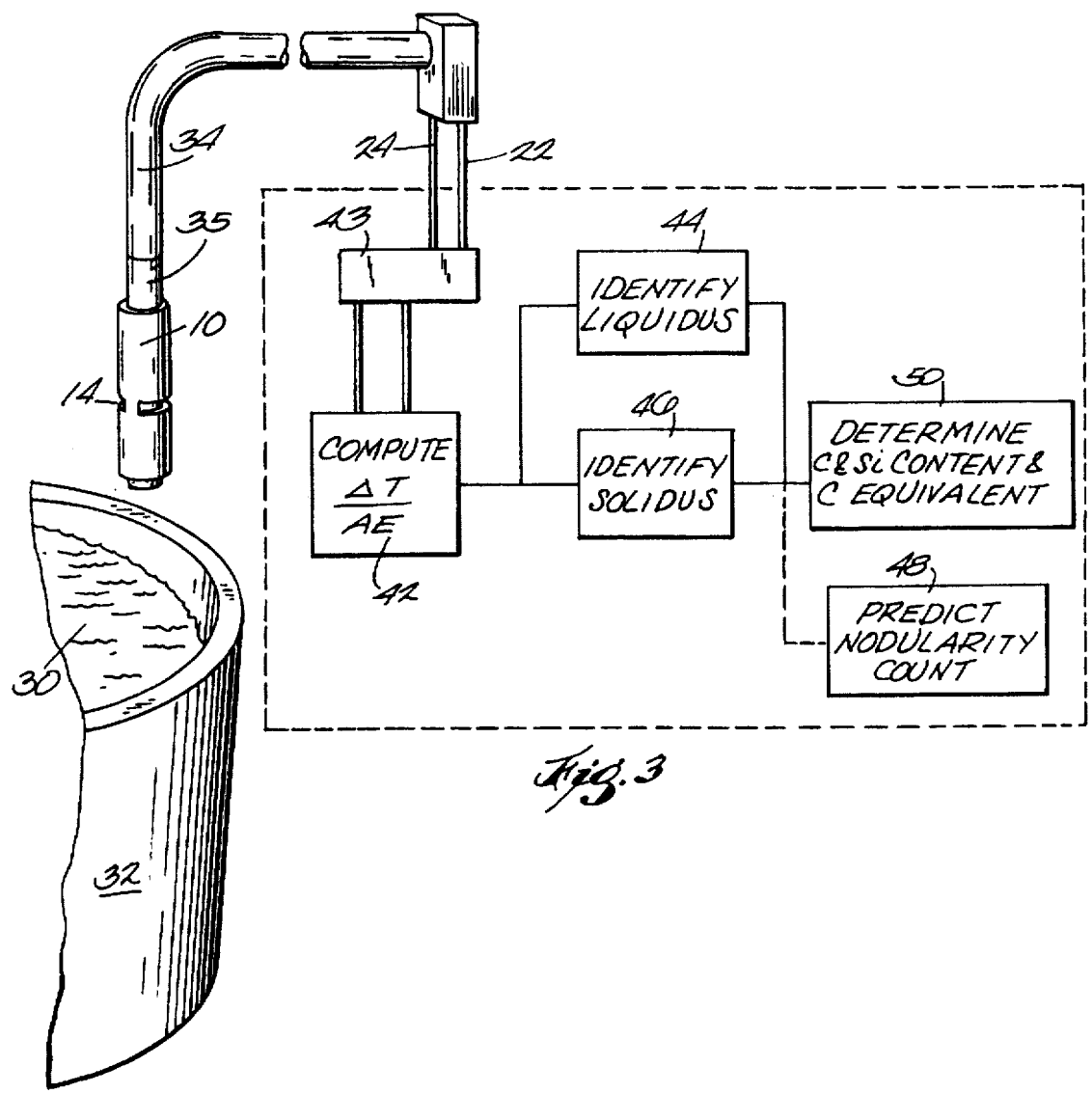
FIG. 3 is a partially schematic view showing the sampling device in conjunction with a vessel containing molten metal and illustrating the steps in the practice in the method of this invention.

Referring to FIG. 1 there is seen a sampling device 10 used in accordance with the invention. Sampling device 10 has a sample chamber 11 preferably defined by a steel sleeve 12. At least one opening 14 preferably positioned above the top of sleeve 12 is provided for inflow of molten metal into sampler 10 upon immersion therein. A plug 16 of heat resistant material such as a sand-resin mixture is used to close the lower end of sampler 10. An outer sleeve 18 of heat resistant insulating material such as refractory fiber is provided to insulate the exterior of sleeve 12, thus avoiding excessive heat transfer into the sample chamber 11 from the molten metal while sampling as well as heat transfer out during cooling. The cooling rate is thus stabilized.

Sampling chamber 11 also houses a temperature measuring device or sensor such as a thermocouple 20. Thermocouple 20 and its connecting wires are also protected by a plug 17 which also may be formed from heat resistant material such as a sand-resin mixture. Lead wires 22 and 24 connect thermocouple 20 of sampler 10 to a supporting lance 34 and temperature monitoring equipment such as a data processor, for example, a microprocessor-based computer 40. The sampler 10 is preferably supported on an appropriate lance 34 or similar device for immersion into molten metal 30 contained in a vessel 32, for example, a ladle. After removal of the sampler 10 from molten metal 30, a sample plug 33 of metal solidifies on cooling.

It will be noted that due to the presence of exteriorly insulated annular sleeve 12, which serves to chill the sample 33, and insulating end plugs 16 and 17, that sample 33 is cooled around its circumference but not at its ends primarily by chill sleeve 12 which serves as an internal cooling material. It is important that the mass of sleeve 12 be sufficiently great relative to that of sample 33 so that upon removal of the mold containing sample 33 from molten iron 30, cooling of the sample 33 will proceed at a rate such that graphite formation and requelescence (ie., temperature increase for a brief time interval), during the cooling period, is prevented in iron of satisfactory quality.

It has been found that in order to cause chilling of sample 33 at satisfactory rate, which enables practice of the invention, the mass of chill sleeve 12 must be between 1.0 and 2.0 times the mass of the sample 33, and more preferably between 1.3 and 1.8. It is also critical that the thermocouple 20 be accurately positioned so that it is displaced radially from the walls of sleeve 12 and longitudinally from plug 16. The mass of sleeve 12, the relative mass of sample 33, the related position of thermocouple 20 and the size of opening 14 and position of plug 16 are all interrelated and important in providing a satisfactory mass of chilling metal effective to cool sample 33 at a rate which provides data usable in the practice of the invention. Sleeve 12 is preferably formed of a steel composition, but other conductive metals, preferably (but not necessarily) having a melting temperature above that of ductile iron may be substituted.

Referring further to FIGS. 1–3, the end of lance 34 is connected to an annular housing/coupling member 35 which carries a male electrical connector plug 36 having thermocouple like metal conductive strips 37 and 38 for attachment to the leads of thermocouple 20. A mating receptacle 39 receives the plug 36. By having the parts 36 and 39 closely interfitting, the sampling assembly 10 can be secured to the lance 34 by means of a friction fit. At the same time, the connection serves as a quick connect coupling between sampler 10 and lance 34. The female connector may be constructed of paper or other heat resistant material.

As shown in FIG. 3, data processor 42 is continually provided with emf signals indicative of temperature readings detected by thermocouple 20. In a preferred embodiment of the invention such readings are obtained at the rate of 7 per second. Generally, it is necessary to use a converter 43 to convert analog signals from thermocouple 20 into digital form which are used by a data processor. Continual computations 42 showing the rate of cooling (in °F. or °C.) are then provided, which may be plotted in graphic form. In accordance with the invention analysis of the cooling rate curve obtained for as short a time period as twenty seconds to one minute enables determination of other important parameters, such as identification of the liquidus point 44 and the solidus point 46. These values then lead to a rapid and accurate determination of carbon content or carbon equivalent 50 for the molten metal 30 (which could not be obtained by prior art procedures from curves 60, 64, 80 & 90). Additionally computation 48 of the estimated nodularity count may be provided. The latter is arrived at empirically based specifically on physical analysis of a significant number of samples and comparing the data thus derived against the rate of cooling curves for the samples and compared against actual nodularity counts and subsequently extrapolating to arrive at an accurate estimate.

In use the sample is dipped in the molten iron for a few seconds, (often 2 to 3 seconds). After removal it is set on a floor or other suitable surface, or suspended in air for cooling. The interior steel wall of the device acts as a heat sink whereas the outer fiber layer protects the sampler from absorbing excessive heat from the molten metal bath during immersion or from losing heat to the ambient atmosphere after withdrawal from the melt. Thus the iron sample is removed in a liquid state with adequate superheat for analysis.

The first derivative determined continuously is the rate of cooling in degrees/second. Rapid cooling caused by the metal surrounding the sample, in effect, prevents requelescence in suitable quality iron. The extremely rapid cooling rate of this invention makes traditional eutectic point reading impossible. However in accordance with the invention the derivative information in the form of a cooling rate curve in degrees/second is easily read. Thus the data processor can provide precise eutectic points determined by the slowing and then an increasing rate of cooling, so long as the cooling rate is not so excessively fast as to cause virtually simultaneous determination of the solidus and liquidus points. The latter situation could occur if excessive chilling of the iron sample were imposed.

Figure 4:
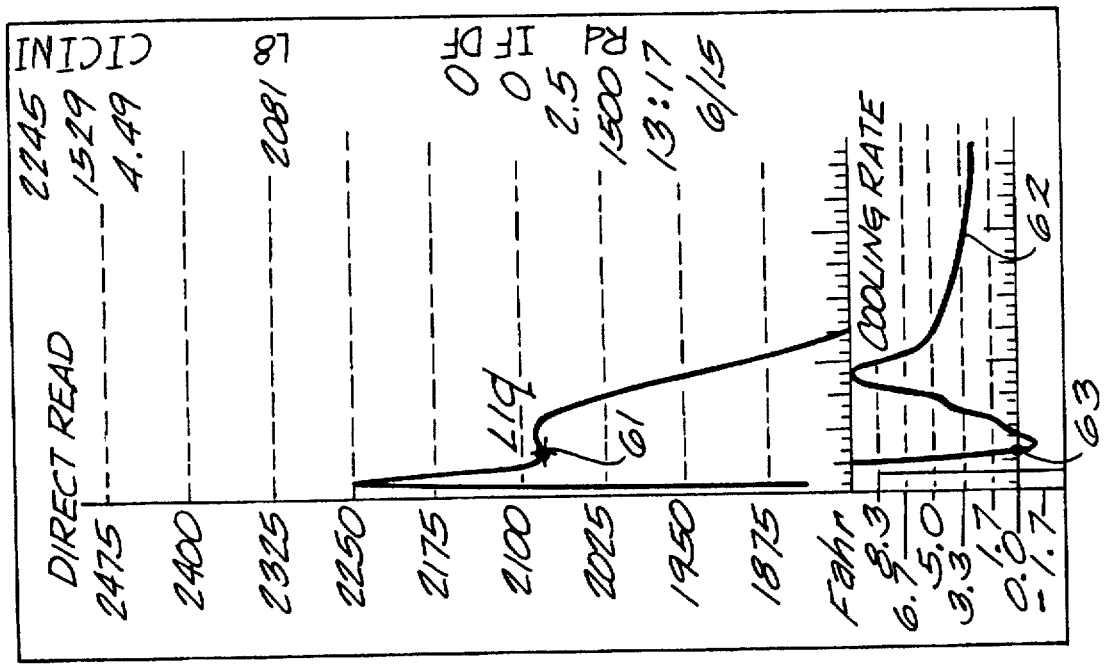
FIG. 4 is a printout including graphs showing a typical recording of temperatures and a derived rate showing change of temperature relative to time and illustrating readings obtained on an unsatisfactory ductile iron sample with a low modularity count.
Figure 5:
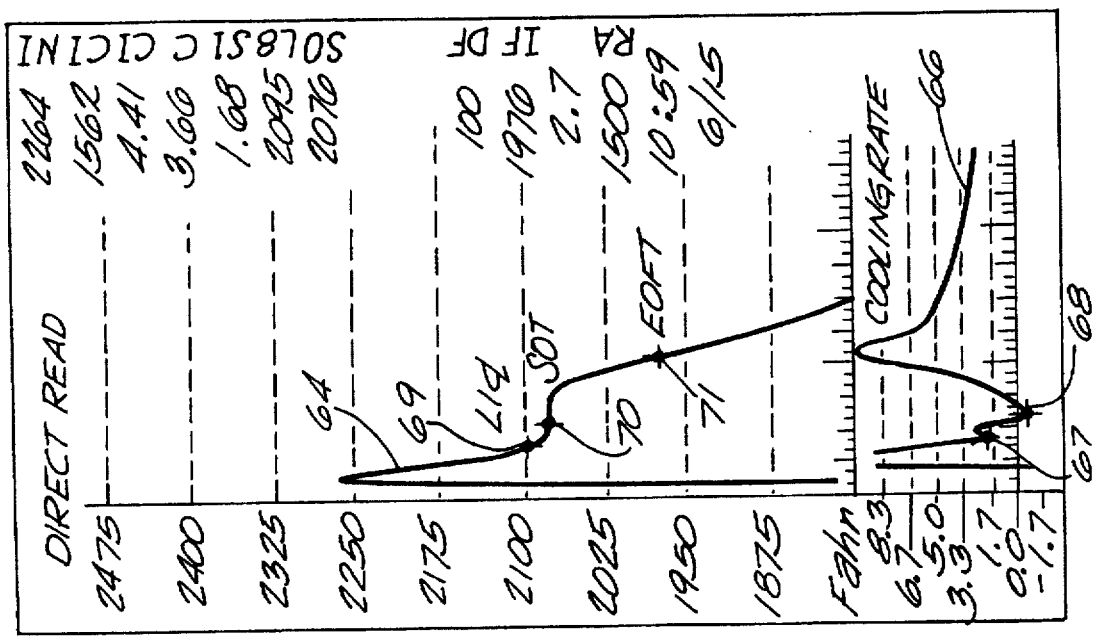
FIGS. 5–7 are printouts similar to that of FIG. 4, but showing readings obtained relative to satisfactory ductile iron samples.

Graphic illustrations 60 and 62 of the directly read temperatures and calculated cooling rates, respectively, are shown in FIG. 4 for an unsatisfactory batch of ductile iron, and similar curves 64 and 66 are shown in FIG. 5 for a suitable batch of ductile iron.

As seen in FIG. 4 of the particular sample tested, which was subsequently also spectrographically analyzed, was found to have excessive carbon content and a low nodularity count. While the temperature curve 60 was not markedly different from the temperature curve 64 of FIG. 5, the rate of cooling curve 62, determined as a first derivative tire of the temperature curve, provides a means for differentiation between the two samples. Note that in the case of FIG. 4 only one drop followed by a rise in the cooling rate occurred, while in FIG. 5 there were two such occurrences.

Referring to FIG. 5, the sample tested therein was found to have a cooling rate curve 66 wherein a first low point 67 occurred after which the cooling rate increased. Subsequently the cooling rate once again slowed to virtually zero at point 68 wherein after the rate once again increased. Point 67, which was reached approximately fifteen seconds after cooling, was initiated was found to be determinative of the liquidus temperature at the corresponding point on curve 64. This point occurred at 2095° F. Point 68 corresponded to the solidus point. Extrapolating this point to the corresponding point on curve 64 provided the information that the solidus point was 2076° F. Point 71 indicated the end of freezing temperature, i.e., the point at which all of the sample was solidified. Utilizing an appropriate algorithm, the determination was made based on the liquidus and solidus temperatures of the sample 69 and 70 that the carbon content of the sample was 3.66 percent while the silicon content was 1.68 percent. The carbon equivalent was determined to be 4.41 percent. All of these values are indicated on the upper right-hand corner of FIG. 5. The additional temperature figures, i.e., 2264° and 1562° are indicative of the temperatures (in °F.) at the beginning and at the end of the analysis which was performed and displayed (end of curve 66).

Figure 6:
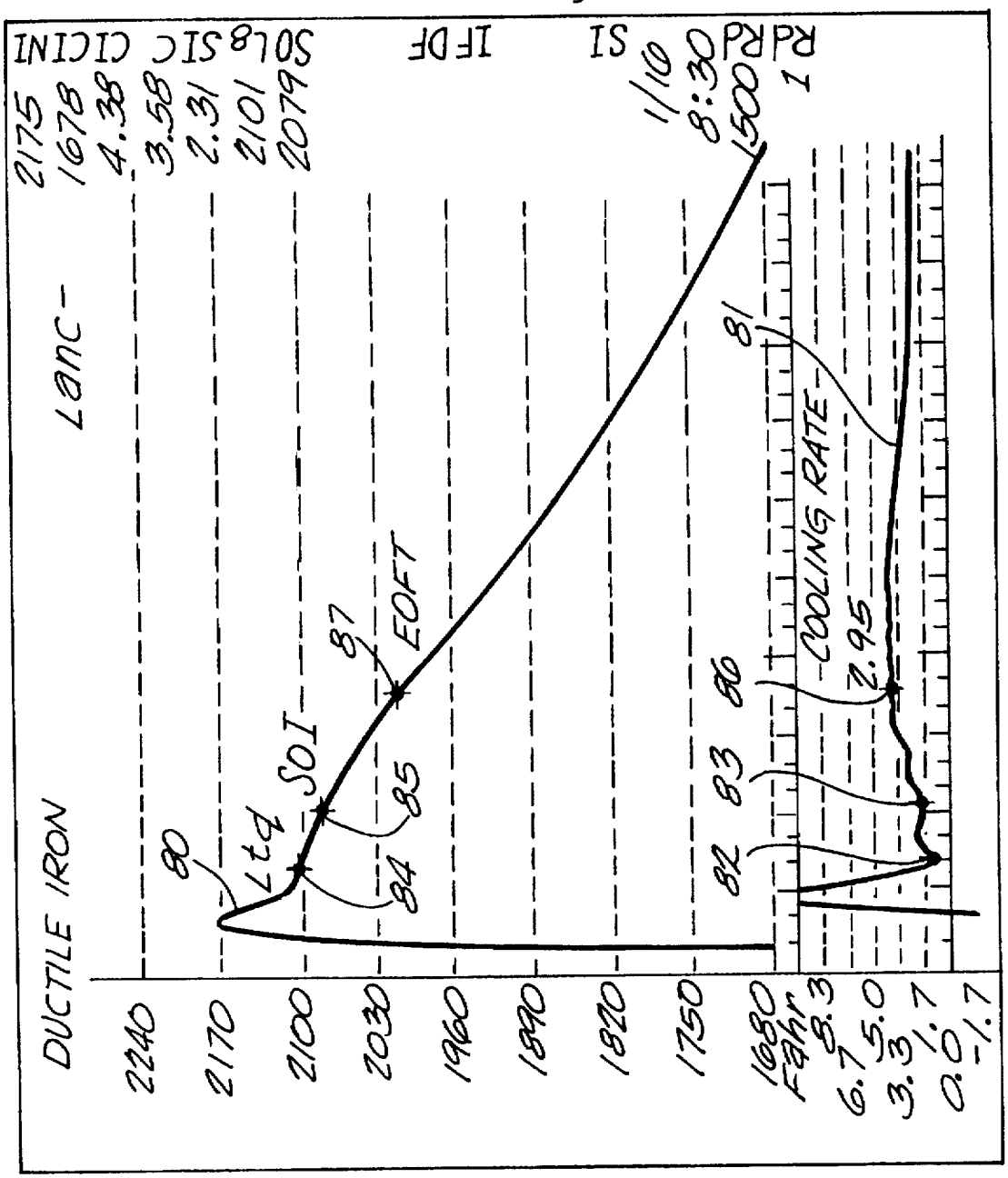
Figure 7:
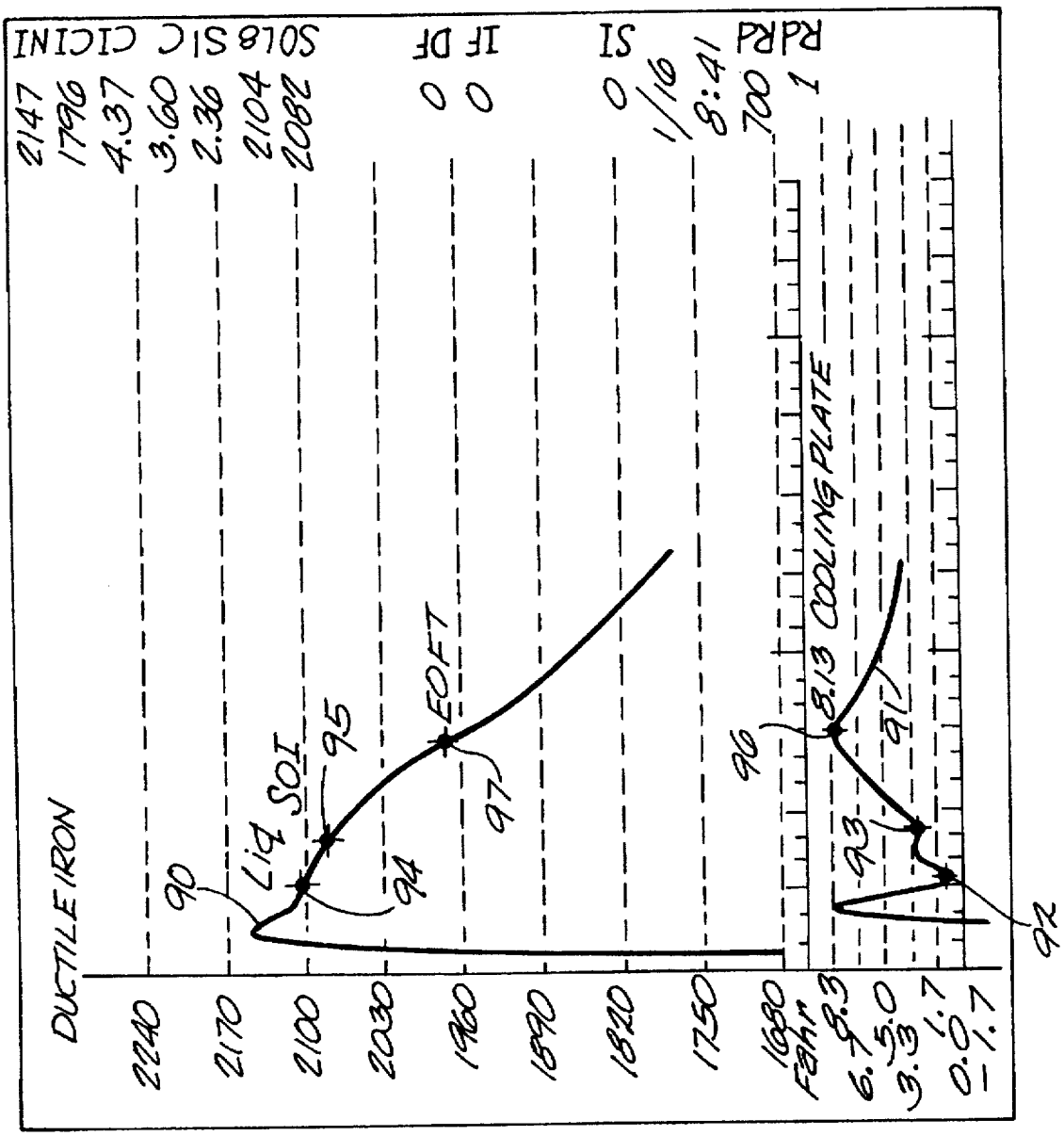

Referring to FIGS. 6 and 7, there are seen temperature plots and cooling rate curves for additional samples of molten iron. FIG. 6 shows a sample that was cooled at a relatively slower rate as can be observed both from the temperature curve 80 and derived cooling rate curve 81. Note that the cooling rate curve included an initial low point 82 after about 25 seconds and a second low point 83 after about 32 seconds with an intermediate time in which the cooling rate increased slightly. Note that a subsequent high point 86 was also obtained which was indicative of the end of freezing temperature point 87. As in the case with the earlier samples, point 82 was indicative of the liquidus temperature of 2101° F. and point 83 was indicative of the solidus temperature 85 which was determined to be 2079° F. The determined carbon equivalent was 4.38 percent, carbon 3.58 percent, and silicon 2.31 percent. As in the case of the earlier samples, these thermal analysis values were very close to those determined by actual laboratory analysis.

The illustrated and preferred embodiments envision the use of microprocessor controlled computer components using digital processing to analyze information and generate feedback signals. It should be appreciated that data processors using other logic control circuits using micro switches, and/or gates, invertors, and the like are equivalent to the microprocessor controlled components and thus may be used instead.

Various features of the invention are set forth in the following claims.

What is claimed is:

1. A direct dip sampler for determination of carbon content of molten iron by thermal analysis comprising a mold chamber a temperature measuring device extending into said chamber;

said temperature measuring device being connected to leads for operative connection thereof to a data processor for continuously registering said temperature and computing the rate of change of said temperature;

at least one fill opening through a side wall of said chamber at a level above the lowest end of said temperature measuring device;

said mold chamber having at least one inner wall of a metal which serves as a heat sink for molten metal introduced into said mold chamber said inner wall substantially surrounding said mold chamber and being adapted to directly contact said molten metal; and, a layer of thermally insulating material surrounding said mold, and insulative plug closing the opposite ends of said mold chamber, whereby heat transfer into and out from said chamber is reduced.

2. A sampler according to claim 1 wherein said temperature measuring device is operatively connected to a data processor, said data processor being adapted to compute the rate of change of temperature over a period of time within said mold and to identify from said measurements significant points in the cooling rate curve of molten metal being analyzed and thereby to compute the carbon content, silicon and carbon equivalent of the molten metal from such measurements.

3. A sampler according to claim 1 wherein said inner wall of metal comprises a steel sleeve which has a mass sufficiently great in relation to the mass of said mold chamber so that cooling of molten iron introduced into said chamber will occur without requelescence thereof.

4. A sampler according to claim 3 wherein said mass is approximately between 1.0 and 2.0 times the mass of an iron sample which fills said mold chamber.

5. A sampler according to claim 4 wherein the ratio of said masses is between 1.3 and 1.8.

6. A sampler according to claim 1 wherein at least one of said plugs is formed of a sand-resin composition which fills a portion of said sleeve.

7. A sampler according to claim 1 wherein said temperature measuring device is a thermocouple located on a central longitudinal axis of said mold chamber.

8. A process of determining carbon content of molten iron comprising providing an expendable analysis device which includes a mold chamber with a temperature measuring device extending therein, said temperature measuring device being connected to leads for operative connection thereof to a data processor for continuously registering said temperature and computing the rate of change of said temperature, at least one fill opening being provided through a side wall of said chamber at a level above the lowest end of said temperature measuring device, said mold chamber having at least one inner wall of a metal which serves as a heat sink for molten metal introduced into said mold chamber, said inner wall substantially surrounding said mold chamber and being adapted to directly contact said molten metal, a layer of non ablative thermally insulating material surrounding said mold, and insulative plugs closing the opposite ends of said mold chamber to control external heat loss;

obtaining a sample from a molten metal bath by direct dipping of said analysis device therein;

removing said sample from said bath into the ambient environment;

continuously measuring and recording the temperature of said sample as it cools;

computing and charting the rate of change of temperature of said sample during said cooling period over a period of time;

observing a first increase in the rate of cooling and recording the temperature at which said rate of change occurred;

observing a subsequent decrease in the rate of cooling;

observing a subsequent second decrease in the rate of cooling and recording the temperature at which said second rate of change occurred; and, deriving a value for the carbon content of said molten metal from said observed changes in rates of cooling.

9. A process according to claim 8 wherein values are also derived for the silicon content and carbon equivalent of said iron.

10. A process according to claim 9 wherein said iron comprises ductile iron.

11. A process according to claim 8 wherein an estimate for the nodularity count of said iron is computed.

12. A method according to claim 8 wherein said first increase in rate of cooling is used to identify the liquidus temperature of said iron and the second increase in temperature is used to identify the solidus temperature of said sample.

13. A direct dip sampler for determination of carbon content of molten iron by thermal analysis comprising a mold chamber which includes a cylindrical steel sleeve adapted for direct contact with molten metal introduced into said mold and which has a vertical longitudinal axis, said sampler being supportable for dipping into molten metal on a reusable lance containing electrical leads;

a thermocouple centrally disposed in said sleeve along said axis;

said thermocouple being connected to said electrical leads for operative connection thereof, through an analog to digital converter, to a data processor for continuously registering temperatures in said chamber and computing the rate of change of said temperature;

a plurality of fill openings through the side wall of said chamber said openings being located on opposite sides of said chamber at a level above the lowest end of said temperature measuring device;

said steel mold chamber serving as a heat sink for molten iron introduced into said mold chamber; and, a layer of thermally insulating refractory material surrounding said mold, and insulative sand resin plugs closing the opposite ends of said mold chamber, whereby heat transfer from molten metal into said chamber is reduced.

14. A sampler according to claim 13 wherein the mass of said sleeve is approximately 1.3 to 1.8 times the mass of iron which fills said mold chamber.

* * * * *